(12) United States Patent
Lecocq et al.

(10) Patent No.: US 11,673,924 B2
(45) Date of Patent: Jun. 13, 2023

(54) PEA PROTEINS WITH IMPROVED FLAVOUR, PRODUCTION METHOD, AND INDUSTRIAL USES

(71) Applicant: ROQUETTE FRERES, Lestrem (FR)

(72) Inventors: Aline Lecocq, Mouvaux (FR); Mathias Ibert, La Chapelle d'Armentieres (FR); Franck Debouverie, Vendin les Bethune (FR)

(73) Assignee: Roquette Freres, Lestrem (FR)

( * ) Notice: Subject to any disclaimer, the term of this patent is extended or adjusted under 35 U.S.C. 154(b) by 457 days.

(21) Appl. No.: 16/645,883

(22) PCT Filed: Sep. 14, 2018

(86) PCT No.: PCT/FR2018/052261
§ 371 (c)(1),
(2) Date: Mar. 10, 2020

(87) PCT Pub. No.: WO2019/053387
PCT Pub. Date: Mar. 21, 2019

(65) Prior Publication Data
US 2020/0277344 A1 Sep. 3, 2020

(30) Foreign Application Priority Data
Sep. 15, 2017 (FR) .................................... 17 58570

(51) Int. Cl.
C07K 14/415 (2006.01)
A23J 1/14 (2006.01)
C07K 1/14 (2006.01)
A23L 33/185 (2016.01)
A61K 38/00 (2006.01)

(52) U.S. Cl.
CPC ............... *C07K 14/415* (2013.01); *A23J 1/14* (2013.01); *A23L 33/185* (2016.08); *C07K 1/145* (2013.01); *A23V 2250/548* (2013.01); *A61K 38/00* (2013.01)

(58) Field of Classification Search
CPC ..... C07K 14/415; C07K 1/145; A23L 33/185; A23J 1/14; A23V 2250/548
USPC .......................................................... 426/634
See application file for complete search history.

(56) References Cited

U.S. PATENT DOCUMENTS 9,259,017 B2    2/2016  Dhalleine et al.
2012/0288588 A1* 11/2012 Barron .................... A23L 7/161
                                                        426/620

FOREIGN PATENT DOCUMENTS

CN          104206644 A     12/2014
CN          105746841 A      7/2016
WO          2015071499 A1    5/2015
WO       WO-2015071499 A1 *  5/2015 ............... A23J 1/14
WO          2017120597 A1    7/2017

OTHER PUBLICATIONS

Sumner, A. K. et al. J. Food Sci. 46: 364-372 (Year: 1981).*
Sosulski, F. et al. Cereal Chem. 56: 533-536 (Year: 1979).*
The English translation of the International Search Report, dated Jan. 8, 2019, in the corresponding PCT Appl. No. PCT/FR2018/052261.

* cited by examiner

*Primary Examiner* — Hamid R Badr

(57) ABSTRACT

The invention relates to pea proteins having improved flavour, a method of producing same involving wet grinding, and the use of these proteins in a food or pharmaceutical composition.

9 Claims, No Drawings

PEA PROTEINS WITH IMPROVED FLAVOUR, PRODUCTION METHOD, AND INDUSTRIAL USES

CROSS-REFERENCE TO RELATED APPLICATIONS

This application is a National Stage Application of PCT/FR2018/052261 filed Sep. 14, 2018, which claims priority from French Patent Application No. 17 58570, filed on Sep. 15, 2017. The priority of said PCT and French Patent Application are claimed. Each of the prior mentioned applications is hereby incorporated by reference herein in its entirety.

FIELD OF THE INVENTION

A subject matter of the present invention is pea proteins, the flavor of which is improved, their process of manufacture, including a wet milling, and the use of these proteins in a food composition or pharmaceutical composition.

PRIOR ART

Daily protein requirements are between 12% and 20% of food intake. These proteins are supplied both by products of animal origin (meat, fish, eggs, dairy products) and by plant foods (cereals, leguminous plants, algae).

However, in industrialized countries, protein intakes are predominantly in the form of proteins of animal origin. However, many studies demonstrate that excessive consumption of proteins of animal origin to the detriment of vegetable proteins is one of the causes of increase in cancers and cardiovascular diseases.

Moreover, animal proteins exhibit many disadvantages, both in terms of their allergenicity, regarding in particular proteins from milk or eggs, and in environmental terms, in connection with the damaging effects of intensive farming.

There thus exists a growing demand from manufacturers for proteins of plant origin having advantageous nutritional and functional properties without, however, exhibiting the disadvantages of compounds of animal origin.

Since the 1970s, the pea has been the leguminous seed plant which has been the most widely developed in Europe and predominantly in France, in particular as protein resource for animal feed but also for food for human consumption. The pea contains approximately 27% by weight of protein matter. The term "pea" is considered here in its broadest sense and includes in particular all wild-type varieties of "smooth pea" and all mutant varieties of "smooth pea" and of "wrinkled pea", irrespective of the uses for which said varieties are generally intended (food for human consumption, animal nutrition and/or other uses). Pea protein, predominantly pea globulin, has been extracted and made economic use of industrially for many years. Mention may be made, as example of pea protein extraction process, of the patent EP 1 400 537. In this process, the seed is milled in the absence of water ("dry milling" process) in order to obtain a flour. This flour will subsequently be suspended in water in order to extract the protein therefrom.

Despite its undeniable qualities, the protein extracted from peas suffers, in comparison with animal proteins, from undesirable flavors, such as "beany" or "vegetable". This flavor is an undeniable brake in many industrial applications, in particular food applications.

Following numerous studies, it has been clearly demonstrated that one of the main causes of these unwanted flavors comes from the synthesis of aldehydes and/or ketones (in particular hexanal) following the action of an internal lipoxygenase on the lipids present in the pea seed, in particular during the extraction of the proteins. Saponins and 3-alkyl-2-methoxypyrazines are also categories of compounds generating these unwanted flavors ("Flavor aspects of pulse ingredients", Wibke S. U. Roland, 2017).

A person skilled in the art has thus developed several solutions which make it possible to improve the flavor of a commercial pea protein and to restore to it a neutral taste. A first solution is based on the masking of the flavor by addition of chemical compounds selected for this purpose: this solution requires the user to introduce, into his formulation, a compound which he does not necessarily want to introduce and which can be a source of regulatory and/or allergenic problems. Another solution is described in the patents U.S. Pat. No. 4,022,919 and WO015267, which have taught from the 1970s that a treatment of said pea protein with water vapor makes it possible to obtain a protein having an improved flavor. Nevertheless, this process can be criticized for the risk of a modification of the functional qualities of the proteins obtained by thermal denaturation (for example the loss of solubility or the increase in its hydration capacity), as well as the need to add a necessary purification stage before use. These solutions can thus be effective but they require the end user of the proteins to carry out additional purification operations liable to modify the practicalities of the pea protein. A person skilled in the art has thus very obviously sought to directly and simply obtain, during its extraction process, a pea protein having an improved flavor.

Numerous potential solutions have been explored including, non-exhaustively, the selection of pea cultivars comprising less lipoxygenase or else the pregermination of the peas prior to the extraction of the proteins. More recently, mention may be made of the patent application WO2017/120597, which describes a process including a precipitation of pea protein by addition of salts, several washing operations and a recovery by centrifugation. Despite a complex process using large amounts of water (which can range up to 30 times the amount of peas), the "pea" and "bitter" flavors are still present in pea protein (see graphs 18A, B and C). Since lipoxygenase and saponins are sensitive to the temperature, the addition of an additional heat treatment during the extraction stage, consisting of heating in a humid environment (otherwise denoted "bleaching" operation), possibly combined with a soaking stage, or dry heating (otherwise denoted "toasting" operation), was obviously worked on. These different solutions are well known in the related soybean sector. An important problem for the pea sector consists of the preservation of pea starch, which must not be degraded in order to be also made economic use of industrially. The soybean does not contain starch: the soybean sector can therefore use very high heating temperatures in order to inhibit lipoxygenase without caring about the starch problem.

The combined use of a tempered heat treatment and of a soaking thus appears the most appropriate solution for the pea sector. Mention may be made, for example, of the patent application WO2015071499, which teaches a process comprising a soaking with lactic acid bacteria at 40° C. Nevertheless, these solutions are not yet satisfactory. This process, which is complex and consumes a large amount of water due to lactic fermentation, still does not make it possible to obtain a pea protein of completely neutral flavor (cf. Table 10, where the smell and/or the taste of peas are noted in each extract).

It is to the credit of the applicant company to have undertaken studies to meet these needs and to have developed the present invention.

A first subject matter of the present invention is a pea protein having a 3-methylbutanal content of greater than 3000 ppb, preferably of greater than 4000 ppb, more preferentially of greater than 5000 ppb.

A second subject matter of the present invention is a process for the extraction of pea proteins comprising the following stages:
a) processing of peas in an aqueous solution, the temperature of which is between 70° C. and 90° C., preferentially between 75° C. and 85° C., more preferentially 80° C., in order to obtain a water/pea suspension;
b) heat treatment of the suspension obtained during stage a), the temperature of said suspension being maintained for 2 to 4 min, preferentially for 3 min;
c) cooling the peas of the suspension obtained during stage b), preferably to a temperature of less than 10° C.;
d) milling the peas resulting from stage c) in an aqueous medium in order to obtain an aqueous suspension of milled peas;
e) extraction of proteins from the aqueous suspension obtained during stage d).

A third subject matter of the present invention is a pea protein obtained by the process of the present invention.

A fourth subject matter of the present invention is the use of a pea protein obtained by the process of the present invention in a food or pharmaceutical composition.

The term "pea" should be understood in the present patent application as meaning all the wild varieties of "smooth pea" and all the mutant varieties of "smooth pea" and of "wrinkled pea".

The term "water" should be understood in the present patent application as meaning all the types of water capable of being used in an industrial environment, in particular in the food-processing industry and in the pharmaceutical industry. Mention may be made, in a nonexhaustive manner, of demineralized water, drinking water and decarbonated water.

The term "protein" should be understood in the present patent application as meaning macromolecules formed of one or more polypeptide chains consisting of the sequence of amino acid residues linked together by peptide bonds. In the specific context of pea proteins, the present invention relates more particularly to globulins (approximately 50-60% of pea proteins) and albumins (20-25%). Pea globulins are mainly subdivided into three subfamilies: legumins, vicilins and convicilins.

The term "flavor" should be understood in the present patent application as meaning all of the oral and nasal sensations which a person experiences when consuming a foodstuff. This flavor can be analyzed and quantified using a trained sensory panel or else by chemical analysis of the compounds known to cause these sensations.

The various subject matters of the invention will be better understood in the detailed description of the invention which follows.

The pea protein which is a subject matter of the present invention is a pea protein having a specific content of certain chemical compounds. Thus, the pea protein according to the invention exhibits a 3-methylbutanal content of greater than 3000 ppb, preferably of greater than 4000 ppb, more preferentially of greater than 5000 ppb.

According to a preferred embodiment, the pea protein can additionally exhibit a specific benzaldehyde content. Thus, the pea protein according to the invention can in particular exhibit a benzaldehyde content of greater than 60 ppb, preferably of greater than 70 ppb.

The pea protein according to the invention can contain between 75% and 95% by weight of proteins, with respect to the weight of dry matter. The dry matter content of the pea protein according to the invention can be between 90% and 99.5% by weight, with respect to the weight of said pea protein before it is dried. Any reference assaying method for quantifying the content of proteins well known to a person skilled in the art can be used. Preferably, the total nitrogen is assayed (in %/crude) and the result is multiplied by the coefficient 6.25. This well-known methodology in the field of vegetable proteins is based on the observation that proteins contain an average of 16% nitrogen. Any method of assaying dry matter well known to a person skilled in the art can also be used.

The pea protein according to the invention can in particular be obtained with the process described below.

The process which is a subject matter of the present invention is a process for the extraction of pea proteins.

The process according to the invention comprises a stage a) of processing peas in an aqueous solution, the temperature of which is between 70° C. and 90° C., in order to obtain a water/pea suspension.

Aqueous solution will be understood as meaning water which can optionally comprise additives, such as in particular antifoaming or bacteriostatic compounds The peas employed in stage a) may have previously undergone stages well known to a person skilled in the art, such as in particular cleaning (removal of unwanted particles, such as stones, dead insects, soil residues, and the like) or even the removal of the external fibers of the pea (external cellulose hull) by a well-known stage called "dehulling".

The amount of peas/amount of aqueous solution ratio in stage a) can in particular be chosen so that the aqueous solution covers all of the peas. Preferentially, the aqueous solution/peas ratio by weight is between 1 and 2.

The temperature of the aqueous solution in stage a) is between 70° C. and 90° C., preferentially between 75° C. and 85° C., more preferentially 80° C. The heating can be carried out using any installation well known to a person skilled in the art, such as an immersed heat exchanger.

The pH of the aqueous solution in stage a) can be adjusted to between 8 and 10, preferentially to 9. The pH can be adjusted by addition of acid and/or base, for example sodium hydroxide or hydrochloric acid. The use of a buffer solution, although not necessary, is conceivable.

The process according to the invention comprises a stage b) of heat treatment carried out by maintaining the temperature of the water/pea suspension obtained in stage a) at between 70° C. and 90° C. for 2 to 4 min, preferentially for 3 min. The temperature can be maintained using any installation well known to a person skilled in the art, such as an immersed heat exchanger.

The heat treatment of the water/pea suspension is preferentially carried out with mechanical stirring, for example by the use of a motorized stirrer, or even under recirculation of the aqueous solution using a pump and a recycling loop.

The process according to the invention comprises a stage c) of cooling the peas of the water/pea suspension obtained during stage b). This is because, on conclusion of stage b), the peas can still reach high temperatures which can be detrimental to certain temperature-sensitive compounds of interest, in particular starch but also vitamins.

According to a preferred embodiment, the cooling stage c) is carried out in a new aqueous solution after draining that used during stages a) and b). Thus, the cooling can in particular be carried out in two stages: the peas are first of all separated from the aqueous solution by any technique known to a person skilled in the art, such as filtration or centrifugation, then they are immersed in a volume of a cold aqueous solution, the temperature of which is between 5° C. and 8° C., for a time which makes it possible to reach the target temperature of the peas of 10° C. *maximum*. In order to lower the temperature, it will optionally be possible to simultaneously use a refrigeration system, for example an immersed tubular exchanger system. The water/pea suspension thus obtained can be used directly during stage d).

The target temperature of the peas of 10° C. can in particular be measured with an infrared thermometer or by introducing a probe thermometer inside the peas.

An alternative mode consists of a direct cooling of the water/pea suspension using a refrigeration system. The target temperature of the peas to be reached is also 10° C. *maximum*.

The process according to the invention comprises a stage d) of milling the peas from stage c) in an aqueous medium in order to obtain an aqueous suspension of milled peas. The peas can be completely covered with aqueous solution originating directly from stage c). An alternative mode consists of the partial or complete draining of the aqueous solution, followed by the milling of the peas with addition of a new aqueous solution in a noncontinuous manner during the milling, for example after the start of the milling, or continuously throughout the duration of the milling.

The milling is carried out by any type of appropriate technology known to a person skilled in the art, such as bead mills, conical mills, helical mills or else rotor/rotor systems.

During the milling, water is added continuously or noncontinuously in order to obtain, at the end of the stage, an aqueous suspension of milled peas titrating between 15% and 25% by weight of dry matter (DM), preferentially 20% by weight of DM, with respect to the weight of said suspension.

At the end of milling, the pH can be checked. Preferably, the pH of the aqueous suspension of milled peas at the end of stage d) is adjusted to between 8 and 10; preferentially, the pH is adjusted to 9. pH correction can be carried out by addition of acid and/or base, for example sodium hydroxide or hydrochloric acid.

The process according to the invention comprises a stage e) of extraction of proteins from the aqueous suspension of stage d). Said extraction can be carried out by any type of appropriate process, such as in particular the precipitation at isoelectric pH of the proteins or also their thermocoagulation by heating. The aim here is to separate the advantageous pea proteins from the other constituents of the aqueous suspension of stage d). Such a process example is, for example, presented in the patent EP 1 400 537 of the applicant company, from section 127 to section 143.

The extraction of the proteins can preferentially be concluded by drying using any technique known to a person skilled in the art. Mention may be made, in a nonlimiting manner, of lyophilization or even atomization. Preferentially, before drying, the pH of the proteins is corrected to 7 by the addition of acids and/or bases, such as hydrochloric acid or sodium hydroxide.

Another subject matter of the present invention is a pea protein capable of being obtained by the extraction process according to the invention. The pea protein obtained according to the process of the invention advantageously exhibits a neutral flavor.

The pea protein obtained with the process of the invention can contain between 75% and 95% by weight of proteins, with respect to the weight of dry matter. The dry matter content of the pea protein obtained by the process of the invention can be between 90% and 99.5% by weight, with respect to the weight of said pea protein, before it is dried. Any reference assaying method for quantifying the content of proteins well known to a person skilled in the art can be used. Preferably, the total nitrogen is assayed (in %/crude) and the result is multiplied by the coefficient 6.25. This well-known methodology in the field of vegetable proteins is based on the observation that proteins contain an average of 16% nitrogen. Any method of assaying dry matter well known to a person skilled in the art can also be used.

In order to quantify the flavors, a first solution consists of the use of an organoleptic tasting panel. There are several standardized protocols in order to qualify and/or quantify the presence and/or absence of certain flavors. One protocol used in the context of this invention is explained in example 2.

It is also possible to evaluate the improvement in the flavor by assaying the compounds known for introducing these unwanted flavors into pea protein. These compounds can, for example, be listed in a nonexhaustive manner:
hexanal;
saponins;
3-alkyl-2-methoxypyrazines;
3-methylbutanal;
benzaldehyde.

A process which makes it possible to quantify the content of these different compounds used in the context of this invention is explained in example 4.

Another subject matter of the present invention is the use of a pea protein obtained by the process according to the invention in a food or pharmaceutical composition.

This is because, due to its neutral flavor, such a pea protein is of a certain advantage in many industrial applications, in particular in the food-processing or pharmaceutical industry, and in animal nutrition.

Food composition is understood to mean a composition intended for the feeding of humans or animals. The term food composition encompasses foodstuffs and food supplements. Pharmaceutical composition is understood to mean a composition intended for a therapeutic use.

The examples which follow make it possible to better illustrate the patent application, without, however, limiting the scope thereof.

EXAMPLE 1: PREPARATION OF A PEA PROTEIN ACCORDING TO THE INVENTION 0.8 kg of peas are employed. The external fibers of the peas are first of all separated from the seeds by crushing (mechanical separation of the external hull and the pea seed) and skin removal (sorting of the external hulls and of the pea seeds using compressed air). The peas are placed in a receptacle containing 1.6 liters of demineralized water heated to 80° C. The temperature of 80° C. is maintained for 3 minutes. The peas are separated from the aqueous solution by filtration on a sieve, the mesh size of which is 2 mm. The peas are subsequently placed for 5 minutes in a second receptacle containing 1.6 liters of demineralized water, the temperature of which is regulated at a temperature of 7° C. This cooling is continued until the temperature of the peas is less than or equal to 10° C. The peas are separated from the aqueous solution by filtration on a sieve, the mesh size of which is 2 mm. The peas, weighing 1.3 kg due to absorption of water, are introduced into the chamber of a mill of Robot Coupe Blixer 4VV type. Milling of the pea is carried out at maximum speed for 1.5 minutes. Then, still while milling at maximum speed, 2.7 liters of demineralized water are added over a period of 3 minutes. Finally, the milling is continued for a period of 0.5 minute. A homogeneous water/pea milled product titrating 20% DM is obtained in the end. This milled product is centrifuged for 5 min at 5000 g. The supernatant, in which the proteins are concentrated, is adjusted to pH 5 and then heated at 60° C. for 10 min in order to cause the proteins to flocculate. The protein flock is recovered by centrifuging at 5000 g for 5 min. The flock is resuspended in a volume of water which makes it possible to obtain a fluid suspension in order to be able to correct its pH to 7 with hydrochloric acid. This flock is subsequently lyophilized. A pea protein titrating 81% protein/DM and 95% DM is obtained. The final product is referenced "Pea protein of the invention according to example 1".

COMPARATIVE EXAMPLE 1: PREPARATION OF A PEA PROTEIN ACCORDING TO THE PRIOR ART WO2015071499

0.8 kg of peas are employed. The external fibers of the peas are first of all separated from the seeds by crushing (mechanical separation of the external hull and the pea seed) and skin removal (sorting of the external hulls and of the pea seeds using compressed air). The peas are then subjected to lactic fermentation in drinking water containing $10^8$ cfu of the *Lactobacillus fermentum* strain. The fermentation was carried out in anaerobic mode, in a closed chamber, containing 400 kg of peas per $m^3$, without degassing, at 40° C., until a pH of 4.2 was reached. The peas are subsequently separated from the fermentation medium by filtration and are then rinsed with an equivalent volume of demineralized water. The peas are introduced into the chamber of a mill of Robot Coupe Blixer 4VV type. Milling of the pea is carried out at maximum speed for 1.5 minutes. Then, while still milling at maximum speed, a certain amount of demineralized water is added over a period of 3 minutes in order to reach approximately 20% DM in the end. Finally, the milling is continued for a period of 0.5 minute. A homogeneous water/pea milled product is obtained. This milled product titrating approximately 20% DM is centrifuged for 5 min at 5000 g. The supernatant, in which the proteins are concentrated, is heated at 75° C. for 15 sec. The supernatant is subsequently adjusted to pH 4.7 in order to obtain an isoelectric flocculation of the proteins. The protein flock is recovered by centrifuging at 5000 g for 5 min. The final product is lyophilized, which product will be referenced "Pea protein of the prior art according to comparative example 1".

COMPARATIVE EXAMPLE 2: PREPARATION OF A PEA PROTEIN ACCORDING TO THE PRIOR ART WO2017120597

90 g of Nutralys® S85F (commercial pea protein isolate) is mixed with 750 g of drinking water in a stirred receptacle. The pH is adjusted to 9 by addition of 6N sodium hydroxide and the mixture is thus stirred for 5 min. A sufficient amount of 4M $CaCl_2$ is subsequently added in order to obtain a concentration of $CaCl_2$ of 30 mM. The pH is subsequently adjusted to 4.6 with 6N hydrochloric acid. The solution is centrifuged for 5 min at 2200 g. The supernatant is removed and the pellet is washed by introduction of an amount of water corresponding to 15 times the weight of pellet. The solution is centrifuged again for 5 min at 2200 g. The pellet is recovered and then lyophilized. The final product will be referenced "Pea protein of the prior art according to comparative example 2".

EXAMPLE 2: METHODOLOGY OF A SENSORY PANEL WHICH MAKES IT POSSIBLE TO DISTINGUISH THE FLAVORS OF PEA PROTEINS

The panel is made up of 30 people who are experts in tasting pea protein in water.
The products were suspended at 5% by weight in Evian® brand water, with 0.3% by weight of sucrose, and homogenized using a hand-held blender.
They are subsequently presented to the panelists at ambient temperature.
The tasting conditions were as follows:
  in the sensory analysis laboratory: individual tasting cubicles, white walls, calm atmosphere (to facilitate concentration);
  white light (to have exactly the same view of the product);
  at the end of the morning or the afternoon (to be at the height of the sensory capabilities);
  products rendered anonymous with a three-figure code (to prevent the code from influencing the assessment of the products);
  products presented in a random order (to prevent order and persistence effects).
The methodology employed to compare the products was Free-Choice Profiling (Williams and Langron, 1984). It is a matter of comparing the products with one another by carrying out a succession of gradings: the panelists choose the descriptors which seem to them to be the most relevant for distinguishing the products from one another and grade the products according to these descriptors, as shown in the table below:

| Sensory descriptor | not perceived 0 | weak 1 | quite weak 2 | medium 3 | quite strong 4 | strong 5 |
|---|---|---|---|---|---|---|
| Pea smell | 457 | | 678 | 910 | | 133 452 |
| ... | | | | | | |

The list of the descriptors presented to the panelists was as follows:

| | | | | |
|---|---|---|---|---|
| acidic | cooked oats | cardboard | *citrus fruits* | butter |
| acidulated bitter | stock cereals | chemical glue | almond floral | fermented cheese |
| astringent | mild | toasted burnt | coconut | yeast |
| spicy | flour | detergent | fresh walnut | rancid |
| salty | milky | metallic | apple | grainy/sandy |
| sweet | pea | paper | wet mop | potato |
| soap | crushed dried pea | dust | earth | vegetable |
| mashed potato | rice | | | |

EXAMPLE 3: CONCLUSIONS OF THE COMPARISON OF THE DIFFERENT PROTEINS

The organoleptic evaluations carried out using the methodology described in example 2 are summarized in the table below.

The products tested are the pea proteins produced according to example 1 and comparative examples 1 and 2, as well as two commercial proteins: Nutralys® S85F and Pisane® B9.

| Sample | Sensory analysis | |
|---|---|---|
| | Pea flavor | Bitter flavor |
| Nutralys ® S85F | 4 | 4 |
| Pisane ® B9 | 4 | 4 |
| Pea protein of the invention according to example 1 | 1 | 1 |
| Pea protein of the prior art according to comparative example 1 | 4 | 4 |
| Pea protein of the prior art according to comparative example 2 | 4 | 4 |

It is observed that the pea protein obtained by the process of the invention exhibits a "pea" flavor and a "bitter" flavor which are much lower than those of the pea proteins of the comparative examples and of the commercial pea proteins tested. The pea protein of the invention can thus be advantageously introduced into a food or pharmaceutical composition as a result of its neutral taste.

EXAMPLE 4: METHODOLOGY FOR ANALYSIS BY ITEX GC/MS IN ORDER TO QUANTIFY THE CONTENT OF 3-METHYLBUTANAL AND BENZALDEHYDE IN THE PEA PROTEIN

Analysis by In-Tube Extraction (ITEX) followed by gas chromatography coupled with mass spectrometry (GC/MS) makes it possible to quantify the contents of volatile organic compounds in the pea protein.

First of all, an extraction of the compounds is carried out with the succession of following stages:

1. 0.5 g of pea protein sample to be analyzed and 10 ml of an acetone/water (80/20) mixture are introduced into a 15 ml vial
2. stirring is carried out at ambient temperature (approximately 20-25° C.) for 30 min and then the mixture is left to separate by settling by leaving to stand
3. the supernatant liquid phase is recovered by filtration on a 0.45 μm filter in a 10 ml vial of headspace type
4. the acetone/water phase is evaporated to dryness under a stream of nitrogen
5. the headspace vial is closed An analysis by ITEX GC/MS is subsequently carried out. The commercial apparatus used is a Bruker Scion SQ 456-GC GC/MS equipped with a CTC CombiPal autosampler with ITEX option.

The ITEX analysis parameters are as follows:
Syringe temperature 100° C.
Trap temperature 40° C.
Incubation temperature 100° C.
Stirring speed 500 rpm
Extraction volume 1000 μl
Extraction number (Extraction strokes) 200
Extraction rate 1000 μl/s
Pull-up delay 2000 ms
Desorption temperature 300° C.
Desorption rate 100 μl/s
Injection rate 100 μl/s
Trap cleaning temperature 300° C.
Trap cleaning time 20 min The GC/MS analysis parameters are as follows:
Column Vf-Wax 30 m*0.25 mm; df 0.25 μm
Prog T° C.: 3 min at 50° C., 5° C./min up to 230° C., 20 min at 230° C.
Split mode injector 1:10 250° C.
Helium: 1 ml/min Finally, the integration of the data obtained on the GC/MS chromatogram is carried out by selectively metering 3-methylbutanal and benzaldehyde. In order to do this, standard samples of these products are used and the procedure is carried out according to the general knowledge of a person skilled in the art.

The results obtained with the commercial samples and with the samples obtained in the preceding examples of this patent application are presented in the table below:

| Sample | ITEX GC/MS analysis (in ppb) | |
|---|---|---|
| | 3-Methylbutanal | Benzaldehyde |
| Nutralys ® S85F | 1614 | 31 |
| Pisane ® B9 | 526 | 37 |
| Pea protein of the invention according to example 1 | 3562 | 68 |
| Pea protein of the prior art according to comparative example 1 | 597 | 24 |
| Pea protein of the prior art according to comparative example 2 | 2022 | 51 |

By correlating the results of the sensory analysis of example 3 and the results obtained by ITEX GC/MS analysis, it is apparent that the sample obtained according to the invention is the only one to exhibit a 3-methylbutanal content of greater than 3000 ppb and a benzaldehyde content of greater than 60 ppb.

It is thus apparent that the proteins exhibiting a high content of 3-methylbutanal and of benzaldehyde have a better organoleptic quality, in particular as regards the "bitter" and "pea" flavors, in comparison with that of the pea proteins of the comparative examples and of the commercial pea proteins tested.

The invention claimed is:

1. A pea protein product, having a 3-methylbutanal content greater than 3000 ppb.

2. The pea protein product as claimed in claim 1, wherein the benzaldehyde content is greater than 60 ppb.

3. A process for the extraction of pea proteins, comprising the steps of:
   a) adding peas to an aqueous solution, the temperature of which is between 70° C. and 90° C. in order to obtain a water/pea suspension;
   b) heat treatment of the suspension obtained during stage a), the temperature of said suspension being maintained between 70° C. and 90° C. for 2 to 4 min;
   c) cooling the peas of the suspension obtained during stage b);
   d) milling the peas resulting from stage c) in an aqueous medium in order to obtain an aqueous suspension of milled peas; and e) extraction of proteins from the aqueous suspension obtained during stage d) so as to separate the proteins from the other constituents of the aqueous suspension of stage d).

4. The process as claimed in claim 3, wherein the cooling stage c) is carried out in a new aqueous solution after draining that used during stages a) and b).

5. The process as claimed in claim 3, wherein the pH of the aqueous solution of stage a) is adjusted to between 8 and 10.

6. The process as claimed in claim 3, wherein the pH of the aqueous suspension of milled peas at the end of stage d) is adjusted to between 8 and 10.

7. A pea protein product, obtained by the extraction process as claimed in claim 3.

8. A food or pharmaceutical composition, comprising the pea protein product according to claim 1.

9. A food or pharmaceutical composition, comprising pea proteins obtained by the extraction process as claimed in claim 3.

* * * * *